United States Patent [19]

Fujisaki et al.

[11] 4,440,749
[45] Apr. 3, 1984

[54] PREVENTIVE AND TREATING AGENT FOR BLOOD LIPIDS ABNORMALITY AND/OR ARTERIOSCLEROSIS

[75] Inventors: Shigemi Fujisaki; Takashi Fujisaki; Junichi Yoshida; Yasuhiro Fujisaki, all of Nishinomiya, Japan

[73] Assignee: Kaken Pharmaceutical Co., Ltd., Tokyo, Japan

[21] Appl. No.: 484,313

[22] Filed: Apr. 12, 1983

[30] Foreign Application Priority Data

Apr. 30, 1982 [JP] Japan .................................. 57-71494

[51] Int. Cl.³ ............................................. A61K 37/48
[52] U.S. Cl. ...................................................... 424/94
[58] Field of Search ........................................... 424/94

[56] References Cited

PUBLICATIONS

Stavrou et al., Chem. Abst. vol. 76 (1972), p. 70754s.
Gemant-Chem. Abst., vol. 72 (1970) p. 41212a.
Nanba et al.-Chem. Abst. vol. 93 (1980), pp. 173, 713h.

*Primary Examiner*—Sam Rosen
*Attorney, Agent, or Firm*—Oblon, Fisher, Spivak, McClelland & Maier

[57] ABSTRACT

A preventive and treating agent for blood lipids abnormally and/or arteriosclerosis comprises a proteolytic enzyme as an effective ingredient.

4 Claims, No Drawings

PREVENTIVE AND TREATING AGENT FOR BLOOD LIPIDS ABNORMALITY AND/OR ARTERIOSCLEROSIS

The present invention relates to a preventive and treating agent for diseases, which comprises a proteolytic enzyme as an effective ingredient. More particularly, the present invention relates to a preventive and treating agent for blood lipids abnormality such as hyperlipemia or hypolipemia and/or arteriosclerosis, which comprises proteolytic enzyme as an effective ingredient.

Blood contains lipids such as cholesterol, triglyceride, phospholipids or free fatty acids. Due to a metabolic disorder, the freeing of cholesterol into blood will increase or decrease, whereby hyperlipemia or hypolipemia will be led. Further, due to metabolic disorder of the connective tissue of the arterial wall, deposition of lipids on the arterial wall is caused, whereby arteriosclerosis such as cerebral arteriosclerosis or coronary arteriosclerosis will be led.

Various medicines have been used for the prevention and treatment of these diseases. However, most of such medicines have side effects. Accordingly, medicines having little side effects have been desired.

The present inventors have found that a proteolytic enzyme is effective for the prevention and treatment of such diseases without bringing about side effects. The present invention is based on this discovery.

Namely, the present invention provides a preventive and treating agent for blood lipids abnormality and/or arteriosclerosis, which comprises a proteolytic enzyme as an effective ingredient.

Now, the present invention will be described in detail with reference to the preferred embodiments.

As the proteolytic enzyme used as the effective ingredient in the present invention, there may be mentioned, for example, trypsin, α-chymotrypsin, bromelain, papain, serrathiopeptidase, seaprose, protease, streptokinase, proctase, pronase, prozyme, urokinase, pancreatin, etc. These enzymes may be used singly or in a suitable combination of two or more.

The preventive and treating agent of the present invention can be administered orally as, for example, tablets, capsules, powders, granules, etc. that are prepared by ordinary techniques of pharmaceutical manufacture or parenterally as, for example, injections, suppositories, ointments, etc. that are prepared in a similar manner. The agent of the present invention can also be used in combination with other pharmaceuticals, for example, other medicines for the liver and kidneys, antibiotics, immunoactivators, antineoplastic agent, hypotensive agent and so forth.

The dosage for attaining the objective, may vary depending on the kind of enzymes, the severity of disorders, methods for administration, dosage forms, etc., but it is usually 1–5,000 mg daily for an adult in the case of the oral administration. Depending on the kind of enzymes, it is preferable to give them as an enteric preparation. The oral dosage attaining the objective is, in terms of an enzyme unit of each enzyme, 20,000–400,000 serrathiopeptidase units in the case of serrathiopeptidase in an enteric preparation, 40,000–800,000 bromelain units in the case of bromelain, 20,000–800,000 units in the case of streptokinase, and 10,000–500,000 tyrosine units in the case of pronase.

PREPARATION EXAMPLE 1

To a mixture of 20 g of pronase and 40 g of lactose is added 10 g of hydroxypropylmethylcellulose. The resulting mixture is made into granules, which are uniformly coated with cellulose acetate phthalate to prepare enteric granules.

PREPARATION EXAMPLE 2

The pronase enteric granules obtained in Preparation Example 1 are filled into capsules to prepare capsule preparations.

CLINICAL EXAMPLE 1

The effect of pronase against hyperlipemia of a patient having a liver disease

Patient: male, born in 1941

Diagnosis: hyperlipemia, chronic hepatitis, chronic nephritis

Blood tests: Abnormal values were recorded from the examinations on lipids, liver functions and kidney functions.

Treatment with pronase: Empinase P (tradename; manufactured by Kaken Chemical Co., Ltd.; each tablet contains 9,000 tyrosine units of pronase) was internally administered in a dosage of 12 tablets per day. As shown in Table 1, the blood tests conducted 49 days later, revealed abnormalities only in AL-P and γ-GTP as liver function indexes and creatinine as a kidney function index, and the lipids values were found to be normal in all items. It was also found that 72 days later, all of the liver functions, kindney functions and lipids values returned to normal levels. No side effects were observed.

TABLE 1

| | | Results of blood tests | | | |
|---|---|---|---|---|---|
| | Normal | Number of days for administration | | | |
| Items examined | values | 0 day | 22 days | 49 days | 72 days |
| GOT | 8–40 | *62 | *52 | 25 | 26 |
| GPT | 5–35 | *38 | 24 | 19 | 19 |
| AL-P | 2.0–10.0 | *15.2 | *13.2 | *11.9 | 9.8 |
| LAP | 70–200 | 154 | 189 | 165 | 155 |
| γ-GTP | –40 | *54 | *84 | *59 | 38 |
| T-CHOL (mg/dl) | 130–230 | *285 | *235 | 186 | 175 |
| E-CHOL (mg/dl) | 80–160 | *180 | *165 | 124 | 124 |
| β-LP (mg/dl) | 150–450 | *583 | *491 | 295 | 225 |
| TRG (mg/dl) | 50–150 | *498 | *264 | 109 | 108 |
| phospholipids (mg/dl) | 150–250 | *265 | *254 | 201 | 203 |
| free fatty acids | 0.17–0.53 | 0.58 | 0.57 | 0.45 | 0.46 |
| total lipids (mg/dl) | 360–960 | *1080 | *981 | 686 | 625 |
| NPN | 20–40 | *42 | *41 | 34 | 34 |
| BU-N | 8–20 | *23 | 20 | 17 | 18 |
| creatinine | 0.7–1.7 | *2.3 | *2.2 | *2.1 | 1.6 |
| uric acid | 2.6–6.0 | *7.0 | *6.8 | 3.0 | 3.1 |

In the Table, the asterisk * indicates an abnormal value.

STATISTIC OBSERVATION 1

The effect of pronase against hyperlipemia and hypolipemia of patients having liver diseases In 14 cases of hyperlipemia and 4 cases of hypolipemia, Empinase P (tradename; manufactured by Kaken Chemical Co., Ltd.; each tablet contains 9,000 tyrosine units of pronase) was internally administered to each patient in a dosage of 12 tablets per day. With respect to each item examined, the number of cases of recovery within three months from the initiation of the administration is shown in Table 2. In 10 cases out of 14 cases of hyperlipemia and in 2 cases out of 4 cases of hypolipemia, the lipids values in all items returned to normal within three months. No side effects were observed.

TABLE 2

| Items examined | Hyperlipemia (14 cases) | | Hypolipemia (4 cases) | |
|---|---|---|---|---|
| | Number of abnormal cases prior to administration | Recovered cases | Number of abnormal cases prior to administration | Recovered cases |
| T-CHOL | 9 | 8 | 4 | 2 |
| E-CHOL | 2 | 2 | 2 | 2 |
| β-LP | 10 | 6 | 1 | 1 |
| TRG | 9 | 5 | 2 | 2 |
| phospholipids | 8 | 8 | 3 | 2 |
| free fatty acids | 3 | 3 | 0 | |
| total lipids | 10 | 7 | 4 | 3 |
| Total | 51 | 39 (76%) | 16 | 12 (75%) |

CLINICAL EXAMPLE 2

The effect of pronase against hyperlipemia of a patient having no liver disease

Patient: female, born in 1931
Diagnosis: hyperlipemia, hypertension
Blood tests: The liver functions and kidney functions were normal. An abnormality was observed in lipids values.
Treatment with pronase: Empinase P (tradename; manufactured by Kaken Chemical Co., Ltd.; each tablet contains 9,000 tyrosine units of pronase) was internally administered in a dosage of 12 tablets per day. As shown in Table 3, the lipids values returned to normal within about three months. No side effects were observed.

TABLE 3

| | Results of blood tests | | | | |
|---|---|---|---|---|---|
| Items examined | Normal values | Number of days for administration | | | |
| | | 0 day | 24 days | 52 days | 92 days |
| GOT | 8–40 | 21 | 23 | 22 | 21 |
| GPT | 5–35 | 18 | 19 | 23 | 18 |
| γ-GTP | −40 | 16 | 17 | 21 | 17 |
| T-CHOL (mg/dl) | 130–230 | *249 | *245 | 223 | 223 |
| E-CHOL (mg/dl) | 80–160 | *172 | 158 | 151 | 153 |
| β-LP (mg/dl) | 150–450 | *532 | *473 | 382 | 445 |
| TRG (mg/dl) | 50–150 | 135 | *158 | *154 | 145 |
| phospholipids (mg/dl) | 150–250 | *268 | 246 | 240 | 241 |
| free fatty acids | 0.17–0.53 | *0.55 | *0.52 | 0.52 | 0.50 |
| total lipids (mg/dl) | 360–960 | *1024 | 946 | 901 | 908 |
| $Cl_2$ | 97–108 | *95 | *95 | *96 | 97 |
| K | 3.4–4.8 | *3.2 | *3.1 | 3.4 | *3.3 |
| NPN | 20–40 | 30 | 32 | 26 | 28 |
| BU-N | 8–20 | 13 | 15 | 16 | 15 |
| creatinine | 0.7–1.7 | 1.2 | 1.4 | 1.5 | 1.3 |
| uric acid | 2.6–6.0 | 4.3 | 5.7 | 6.0 | 5.9 |

In the Table, the asterisk * indicates an abnormal value.

STATISTIC OBSERVATION 2

The effect of pronase against hyperlipemia and hypolipemia of patients having no liver diseases In 13 cases of hyperlipemia and 2 cases of hypolipemia of patients having no liver diseases, Empinase P (tradename; manufactured by Kaken Chemical Co., Ltd.; each tablet contains 9,000 tyrosine units of pronase) was internally administered to each patient in a dosage of 12 tablets per day. With respect to each item examined, the number of cases of recovery within three months from the initiation of the administration is shown in Table 4. In 11 cases out of 13 cases of hyperlipemia and in 1 case out of 2 cases of hypolipemia, the lipids values in all items returned to normal within three months. No side effects were observed.

TABLE 4

| Items examined | Hyperlipemia (14 cases) | | Hypolipemia (4 cases) | |
|---|---|---|---|---|
| | Number of abnormal cases prior to administration | Recovered cases | Number of abnormal cases prior to administration | Recovered cases |
| T-CHOL | 10 | 8 | 2 | 2 |
| E-CHOL | 6 | 4 | 2 | 1 |
| β-LP | 3 | 3 | 1 | 0 |
| TRG | 3 | 3 | 1 | 1 |
| phospholipids | 4 | 4 | 2 | 2 |
| free fatty acids | 1 | 1 | 0 | |
| total lipids | 3 | 2 | 2 | 2 |
| Total | 30 | 25 (83%) | 10 | 8 (80%) |

CLINICAL EXAMPLE 3

The effect of pronase against cerebral arteriosclerosis (1)

Patient: male, born in 1921
Diagnosis: cerebral arteriosclerosis, hyperlipemia, chronic nephritis
Present condition: The patient was attacked by cerebral apoplexy three years ago. The I, II and III branches of the facial nerve on the right hand side were all paralyzed. Phonation was possible but the speech was unclear. An equilibrium function test and a Mann's standing up test revealed that he tended to tumble toward the right hand side and showed a walking deflection toward the right hand side, thus showing nystagmus preferential towards the left hand side. A light right-side hemiplegia was observed. In the blood test, hyperlipemia was observed. (see Table 5)
Treatment with pronase: Empinase P (tradename; manufactured by Kaken Chemical Co., Ltd.; each tablet contains 9,000 tyrosine units of pronase) was internally administered in a dosage of 12 tablets per day. By 47th day, he was recovered from the walking deflection and paralyzed walking which used to be scaresely recovered, and the I branch of the facial nerve on the right hand side started to recover.
By 78th day, the lipids values were all recovered to normal and the kidney functions returned to normal, and at the same time, the preferential nystagmus disappeared and substantial recovery was observed in the right-side hemiplegia and the walking trouble. Further, the speech became fairly clear. No side effects were observed.

TABLE 5

| | Results of blood tests | | | |
|---|---|---|---|---|
| Items examined | Normal values | Number of days for administration | | |
| | | 0 day | 47 days | 78 days |
| T-CHOL (mg/dl) | 130–230 | *247 | 226 | 205 |
| E-CHOL (mg/dl) | 80–160 | *175 | 155 | 130 |
| β-LP (mg/dl) | 150–450 | *538 | 440 | 430 |
| TRG (mg/dl) | 50–150 | *238 | *185 | 145 |
| phospholipids (mg/dl) | 150–250 | *265 | 246 | 230 |
| free fatty acids | 0.17–0.53 | *0.58 | 0.53 | 0.46 |
| total lipids (mg/dl) | 360–960 | *1050 | 958 | 920 |
| $Cl_2$ | 97–108 | 103 | 102 | 103 |

TABLE 5-continued

| | Results of blood tests | | | |
|---|---|---|---|---|
| | Normal | Number of days for administration | | |
| Items examined | values | 0 day | 47 days | 78 days |
| Na | 136–147 | 141 | 141 | 142 |
| K | 3.4–4.8 | 4.1 | 4.1 | 4.1 |
| Ca | 4.2–5.7 | 4.5 | 4.6 | 4.6 |
| NPN | 20–40 | *42 | 40 | 38 |
| BU-N | 8–20 | *22 | 20 | 18 |
| creatinine | 0.7–1.7 | *2.1 | *2.1 | 1.7 |
| inorganic phosphorus | 2.5–4.5 | *2.4 | 2.5 | 2.6 |
| uric acid | 2.6–6.0 | *6.5 | *6.8 | *6.3 |

In the Table, the asterisk * indicates an abnormal value.

CLINICAL EXAMPLE 4

The effect of pronase against cerebral arteriosclerosis (2)

Patient: male, born in 1910

Diagnosis: cerebral arteriosclerosis, chronic hepatitis, chronic nephritis, hyperlipemia, vertigo Present condition: The patient had a spasm of cerebral apoplexy four months ago. The right forearm was paralyzed for exercise and the right lower extremity was paralyzed for walking, i.e. a light right-side hemiplegia was observed. From an equilibrium function test, nystagmus preferential towards the right hand side was observed, thus indicating a left-cerebral circulation disorder. In the blood tests, the liver functions and kidney functions showed abnormal values, as shown in Table 6. Hyperlipemia was also observed.

Treatment with pronase: Empinase P (tradename: manufactured by Kaken Chemical Co., Ltd.; each tablet contains 9,000 tyrosine units of pronase) was internally administered in a dosage of 12 tablets per day. By 85th day after the initiation of the administration, the liver functions returned almost to normal except for GOT and γ-GTP; the lipids values returned to normal except for triglyceride; and the kidney functions returned to normal except for uric acid. By 108th day, the liver functions, kidney functions, and lipids values returned to normal. Further, the vertigo and nystagmus disappeared, and the substantial recovery from the paralysis of the hand and leg was observed. No side effects were observed.

TABLE 6

| | Results of blood tests | | | |
|---|---|---|---|---|
| | Normal | Number of days for administration | | |
| Items examined | values | 0 day | 52 days | 85 days | 108 days |
| GOT | 8–40 | *101 | *83 | *46 | 40 |
| GPT | 5–35 | *68 | *45 | 34 | 32 |
| AL-P | 10–20 | *16.3 | *12.6 | 9.8 | 8.6 |
| LAP | 70–200 | *203 | 184 | 170 | 190 |
| γ-GTP | –40 | *84 | *55 | *43 | 38 |
| T-CHOL (mg/dl) | 130–230 | *326 | 220 | 213 | 198 |
| E-CHOL (mg/dl) | 80–160 | *189 | 156 | 125 | 126 |
| β-LP (mg/dl) | 150–450 | *623 | 450 | 420 | 415 |
| TRG (mg/dl) | 50–150 | *521 | *283 | *156 | 150 |
| phospholipids (mg/dl) | 150–250 | *275 | 232 | 222 | 204 |
| free fatty acids | 0.17–0.53 | *0.58 | *0.56 | 0.52 | 0.41 |
| total lipids (mg/dl) | 360–960 | *1230 | *972 | 842 | 788 |
| NPN | 20–40 | *42 | 40 | 35 | 35 |
| BU-N | 8–20 | *23 | *21 | 18 | 17 |
| creatinine | 0.7–1.7 | 1.7 | 1.5 | 1.4 | 1.3 |

TABLE 6-continued

| | Results of blood tests | | | |
|---|---|---|---|---|
| | Normal | Number of days for administration | | |
| Items examined | values | 0 day | 52 days | 85 days | 108 days |
| uric acid | 2.0–6.0 | *6.8 | *6.8 | *6.8 | 6.0 |

In the Table, the asterisk * indicates an abnormal value.

CLINICAL EXAMPLE 5

The effect of pronase against coronary arteriosclerosis

Patient: male, born in 1919

Diagnosis: coronary arteriosclerosis, myocardial infarction, hyperlipemia, vertigo Present condition: The patient has been suffering vertigo and nausa since four to five years ago. He felt pressure at the chest and tackysystole even when he did not feel vertigo. The equilibrium function test revealed hystagmus preferential towards the right hand side and a tumbling reaction towards the left, thus indicating left cerebral blood circulation disorder. From the electrocardiogram, left ventricular frontal wall arteriosclerosis (thrombosis) and nyocardial disorder were observed. As shown in Table 7, from the blood tests, the liver functions and kidney functions were found to be normal, but hyperlipemia was observed.

Treatment with pronase: Empinase P (tradename; manufactured by Kaken Chemical Co., Ltd.; each tablet contains 9,000 tyrosine units of pronase) was internally administered in a dosage of 12 tablets per day. By 72nd day, the lipids values were all recovered to normal. At the same time, the tachysystole and pressure at the chest disappeared, and the electrocardiogram was also substantially improved. No side effects were found.

TABLE 7

| | Results of blood tests | | | |
|---|---|---|---|---|
| | Normal | Number of days for administration | | |
| Items examined | values | 0 day | 39 days | 72 days | 102 days |
| GOT | 8–40 | 16 | 15 | 16 | 14 |
| GPT | 5–35 | 18 | 23 | 22 | 21 |
| γ-GTP | –40 | 21 | 25 | 23 | 26 |
| T-CHOL (mg/dl) | 130–230 | *253 | 216 | 192 | 153 |
| E-CHOL (mg/dl) | 80–160 | *176 | 151 | 125 | 126 |
| β-LP (mg/dl) | 150–450 | *558 | 438 | 426 | 440 |
| TRG (mg/dl) | 50–150 | *245 | *256 | 150 | 143 |
| phospholipids (mg/dl) | 150–250 | *266 | 232 | 215 | 221 |
| free fatty acids | 0.17–0.53 | *0.57 | 0.48 | 0.45 | 0.46 |
| total lipids (mg/dl) | 360–960 | *1130 | 942 | 830 | 845 |
| NPN | 20–40 | 28 | 30 | 31 | 27 |
| BU-N | 8–20 | 12 | 16 | 15 | 13 |
| creatinine | 0.7–1.7 | 1.2 | 1.4 | 1.3 | 1.3 |
| uric acid | 2.6–6.0 | 4.2 | 4.2 | 4.2 | 4.2 |

In the Table, the asterisk * indicates an abnormal value.

As is evident from foregoing Clinical Examples, pronase was found to exhibit remarkable effectiveness in the treatment of hyperlipemia, hypolipemia and arteriosclerosis and no side effects were observed.

We claim:

1. A method of preventing or treating blood lipids abnormality comprising administering to a patient in need of such therapy an effective amount of pronase or serrathiopeptinase to prevent or treat said blood lipids abnormality.

2. The method of claim 1 wherein pronase is formulated in the form of an enteric preparation.

3. The method of claim 2 wherein the pronase enteric preparation is orally administered in a dosage of from 10,000 to 500,000 tyrosine units daily for an adult.

4. The method of claim 1 wherein the blood lipids abnormality is hyperlipemia or hypolipemia.

* * * * *